United States Patent [19]

Deschler et al.

[11] Patent Number: 5,122,609
[45] Date of Patent: Jun. 16, 1992

[54] SUBSTITUTED ORGANYLOXYSILYL-FUNCTIONAL, CYCLIC THIOUREAS

[75] Inventors: Ulrich Deschler; Peter Kleinschmit, both of Hanau, Fed. Rep. of Germany

[73] Assignee: Degussa Aktiengesellschaft, Fed. Rep. of Germany

[21] Appl. No.: 639,280

[22] Filed: Jan. 10, 1991

Related U.S. Application Data

[62] Division of Ser. No. 357,723, May 26, 1989, Pat. No. 5,010,203.

[30] Foreign Application Priority Data

Jun. 25, 1988 [DE]  Fed. Rep. of Germany ....... 3821464

[51] Int. Cl.$^5$ .............. C07F 7/10; C07F 7/18
[52] U.S. Cl. .................. 548/110; 544/229; 540/202; 540/487
[58] Field of Search ......... 548/110; 544/229; 540/202, 487

[56] References Cited

U.S. PATENT DOCUMENTS 2,767,143  10/1956  Caffrey et al. ............. 548/110
2,853,513  9/1958  McKay et al. ............. 548/110

Primary Examiner—Mary C. Lee
Assistant Examiner—Joseph K. McKane
Attorney, Agent, or Firm—Cushman, Darby & Cushman

[57] ABSTRACT

Novel cyclic N,N,N' and N,N,N',N'-substituted organyloxysilyl-functional silanes are prepared by reacting an aminopropyl silane with carbon disulfide and heating the dithiocarbamate.

1 Claim, 1 Drawing Sheet

SUBSTITUTED ORGANYLOXYSILYL-FUNCTIONAL, CYCLIC THIOUREAS

This is a division of application Ser. No. 07/357,723, filed May 26, 1989, now U.S. Pat. No. 5,010,203, issued Apr. 23, 1991.

The present invention relates to cyclic N,N,N' and N,N,N',N'-substituted organyloxysilyl-functional thioureas and a method of preparing them.

BACKGROUND OF THE INVENTION

The reaction of aminopropyl trialkoxysilanes with alkyl isothiocyanates is known from A. Baigozhin, Zh. Obshch. Khim. 43 (1973), p. 1408 (C.A. 79: 66463r), which results in N, N'-disubstituted thioureas of the formula $(RO)_3Si-(CH_2)_3-NH-CS-NH-R'$, in which R = ethyl and
R' = phenyl, allyl.

A symmetric N, N'-substituted compound is described by M. G. Voronkov et al. in Zh. Obshch. Khim. 54 (1984), p. 1098 (C.A. 101: 192031j).

It is obtained by means of the reaction of aminopropyl trialkoxysilanes with thiourea $$((RO)_3Si-(CH_2)_3-NH-CS-NH-(CH_2)_3-Si(OR)_3).$$

SUMMARY OF THE INVENTION

The object of the present invention is to provide a method of preparing new, substituted trialkoxysilyl-functional thioureas which permits the use of readily available starting materials and produces the desired compounds in good yields. A further object of the invention is to provide novel thioureas and novel dithiocarbamate intermediates useful for making the said thioureas.

These and other objects are achieved in a method of preparing cyclic N,N,N' and N,N,N',N'-substituted organyloxy-functional thioureas, in which a) An aminopropyl silane of the general formula (I)

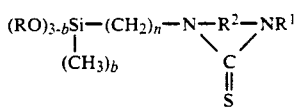

in which n represents a number in the range 1 to 6, especially 1 or 3

R represents alkyl with 1 to 6 carbon atoms, cycloalkyl with 5 to 7 atoms or aryl R¹ represents hydrogen or

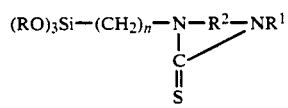

R² represents an alkylene group having 1 to 4 carbon atoms, especially —CH₂—CH₂—, or arylene, especially 1,2-phenylene, b represents 0,1 or 2, preferably 0 is reacted with carbon disulfide in an organic solvent, b) The precipitated, optionally separated dithiocarbamate of the formula (II)

 II is heated until no more hydrogen sulfide is released and the resulting product of the general formula (III)

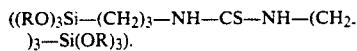 III is separated by conventional methods.

The preparation of the cyclic thioureas thus takes place according to the following basic scheme:

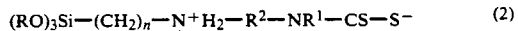 (1)

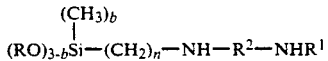 (2)

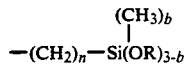

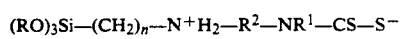

The reaction according to equation (1) is preferably performed in an inert, non-polar, aprotic solvent, preferably in tetrahydrofuran.

The following are also suitable as solvents: (Halogenated) hydrocarbons such as e.g. n-pentane or hydrogen tetrachlorides, (cyclic) ethers such as e.g. diethyl ether, diethylene glycol dimethyl ether or dioxane as well as their mixtures.

The diamine-functional organosilanes used as starting materials for the first step are generally known or can be prepared according to known methods, e.g. by means of the method described by J. L. Speier et al., J. Org. Chem. 36 (1971) pp. 3120 ff.

The reaction temperatures are preferably below the boiling point of carbon disulfide, especially at temperatures from 0° to 45° C. On account of the exothermic formation of the dithiocarbamate, this requires an external or internal cooling of the reaction mixture which may be achieved by known methods.

It is advantageous to proceed as follows: 1 to 1.2, preferably 1.1 moles carbon disulfide are dissolved in a suitable organic solvent per mole diamino organosilane according to formula (I). The solution is placed in a receiver and the silane is added drop-by-drop with external cooling and monitoring of the temperature.

A dithiocarbamate according to formula (II) precipitates toward the end of the addition of silane. However, it is not necessary to isolate this dithiocarbamate in order to obtain the cyclic thioureas according to formula (III). The reaction solution obtained according to equation (1) can be directly treated thermally in order to split off hydrogen sulfide. In this instance, polar, aprotic solvents such as e.g. N,N-dimethyl formamide or even such polar, protic solvents which do not prevent a rapid formation of the dithiocarbamates, such as e.g. alcohols (especially ROH in which R has the meaning given above) are also suitable for carrying out the reaction according to equation (1).

It is preferable to combine distillation of the solvent with the reaction according to equation (2). That means that the temperature during step (2) is above the boiling point of the particular solvent used at normal pressure, especially in a range from 30° to 140° C.

After removal of the solvent, the reaction mixture is generally reheated for 0.5 to 2 hours to 110° C. It has proven to be especially advantageous to thoroughly flush the reaction solution with nitrogen during this step in order to expedite stripping of hydrogen sulfide which is liberated. However, as an alternative, complete removal of the hydrogen sulfide from the reaction mixture can also be achieved by applying a vacuum of e.g. 15 mbars.

The novel thioureas of the present invention are N,N,N' and N,N,N',N'-substituted, cyclic thioureas of the general formula (III)

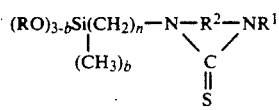       III in which n, R, $R^1$ and $R^2$ have the meanings given above. These compounds are useful as vulcanization accelerators in halogen rubbers.

BRIEF DESCRIPTION OF FIGURE OF DRAWING

The drawing gives the $^1H$—NMR spectrum of

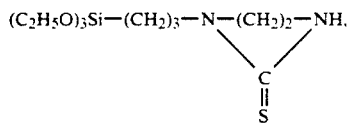       (2)

DETAILED DESCRIPTION OF PREFERRED EMBODIMENTS

Figure 1:
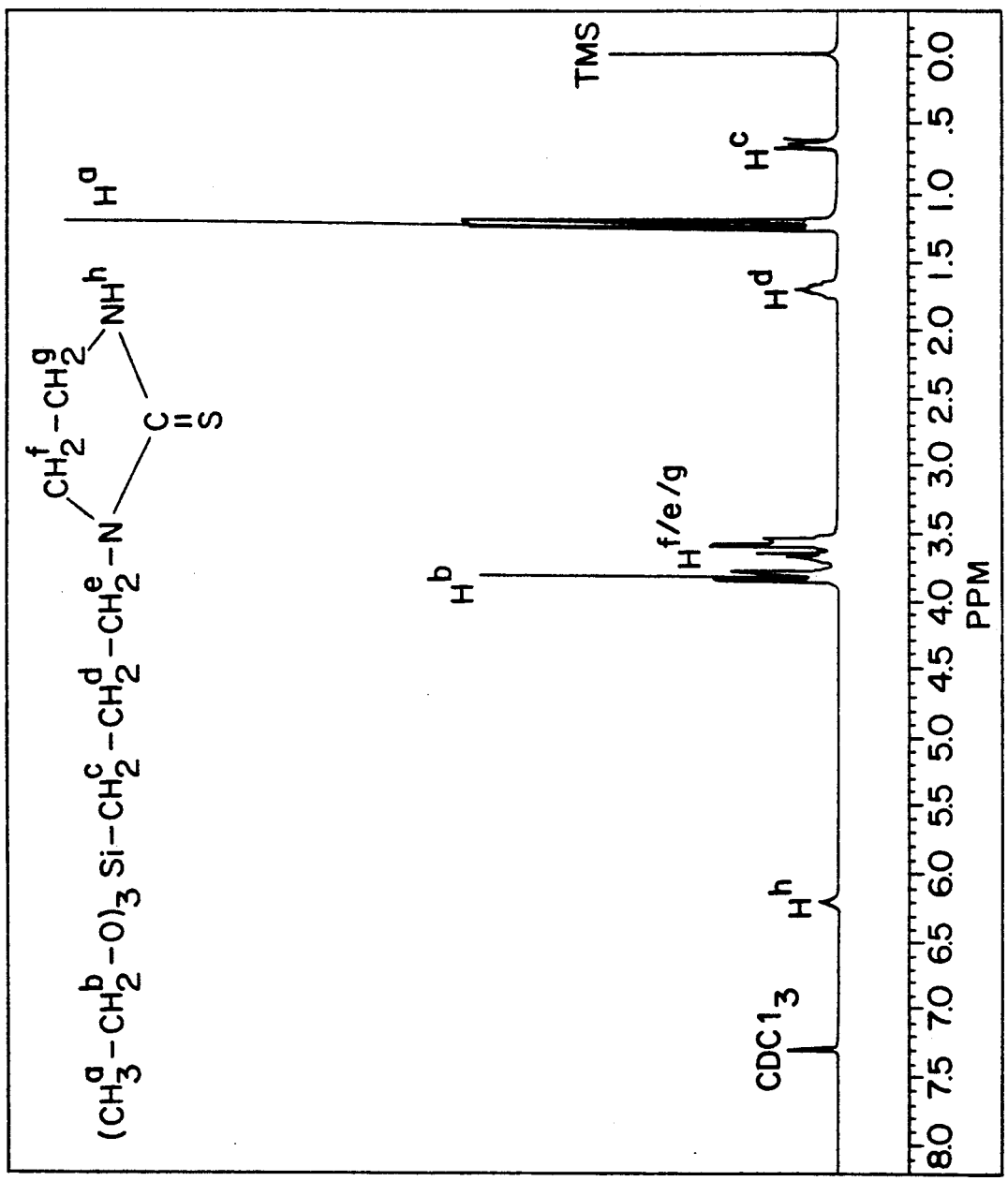

The following examples illustrate the invention. I. Cyclic N-(3-trialkoxysilylpropyl)-thioureas (Examples 1-3):

General method for preparation: In Examples 1-3, 1.1 moles carbon disulfide per mole diamino organosilane are placed in a receiver in 250 ml tetrahydrofuran and the silane is added dropwise with external cooling over a period of 0.5 hour. The dithiocarbamate precipitates toward the end of the addition of silane as a zwitterion in the form of a bright yellow, crystalline powder which does not, however, need to be isolated prior to the thermal splitting off of hydrogen sulfide. This thermal treatment is achieved advantageously by distilling off the solvent under normal pressure and by subsequent heating for 1.5 hours at 110° C., while the reaction mixture is washed thoroughly with nitrogen for a more rapid removal of the hydrogen sulfide which is liberated.

EXAMPLE 1

N—(3-trimethoxysilylpropyl)—N,N'-ethylene thiourea,

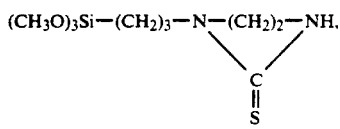       (1)

is prepared from 111.2 g N—(3-trimethoxysilylpropyl)ethylene diamine (0.5 mole) and 41.9 g carbon disulfide (0.55 mole, excess);

Yield: 128.9 g corresponding to 97.5 % of theory; yellow, crystalline solid: $C_9H_{20}N_2O_3SSi$ (264, 420)

|        | C (%) | H (%) | N (%) | S (%) |
|--------|-------|-------|-------|-------|
| calc.: | 40.88 | 7.62  | 10.59 | 12.13 |
| obs.:  | 40.2  | 7.7   | 10.1  | 11.7  |

EXAMPLE 2

N—(3-triethoxysilylpropyl)-N,N'ethylene thiourea,

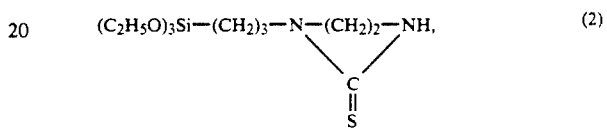       (2)

is prepared from 365.5 g N—(3-triethoxysilylpropyl)ethylene diamine (1.38 moles) and 115.7 g carbon disulfide (1.52 moles, excess):

Yield: 416.5 g corresponding to 98.5 % of theory; yellow, crystalline solid; $C_{12}H_{26}N_2O_3SSi$ (306, 501)

|        | C (%) | H (%) | N (%) | S (%) |
|--------|-------|-------|-------|-------|
| calc.: | 47.03 | 8.55  | 9.14  | 10.46 |
| obs.:  | 46.3  | 8.6   | 9.3   | 9.9   |

The 1H—NMR spectrum of (2) is shown in the drawing.

EXAMPLE 3

N—(3-triethoxysilylpropyl)—N,N'-o-phenylene thiourea,

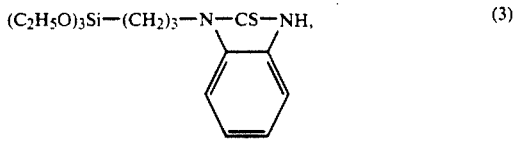       (3)

is prepared from 109.3 g N-(3-triethoxysilylpropyl)-o-phenylene diamine (0.35 mole) and 29.3 g carbon disulfide (0.39 mole, excess):

Yield: 121.9 g corresponding to 98,3 % of theory: yellow, crystalline solid; $C_{16}H_{26}N_2O_3SSi$ (353, 546)

|        | C (%) | H (%) | N (%) | · S (%) |
|--------|-------|-------|-------|---------|
| calc.: | 54.20 | 7.39  | 7.90  | 9.04    |
| obs.:  | 53.7  | 7.8   | 7.4   | 8.2     |

II Cyclic N,N'-bis(3-trialkoxysilylpropyl)-thioureas (Examples 4,5):

General method for preparation: The preparation takes place exactly as described for examples 1-3, with the exception that, instead of the mono silylpropyl-substituted diamines, the corresponding N,N'-disilylpropyl-substituted amines are used.

EXAMPLE 4

N,N'-bis(3-triethoxysilylpropyl)-N,N'-ethylene urea, $$(C_2H_5O)_3Si-(CH_2)_3-N-(CH_2)_2-N-(CH_2)_3-Si(OC_2H_5)_3, \quad (4)$$
$$\diagdown \underset{\underset{S}{\parallel}}{C} \diagup$$

is prepared from 117.2 g N,N'-bis(3-triethoxysilylpropyl) ethylene diamine (0.25 mole) and 20.9 g carbon disulfide (0.28 mole);

Yield: 121.8 g corresponding to 95.4 % of theory;

orangish brown, crystalline solid; $C_{21}H_{46}N_2O_6SSi_2$ (510, 843)

|  | C (%) | H (%) | N (%) | S (%) |
| --- | --- | --- | --- | --- |
| calc.: | 49.38 | 9.08 | 5.48 | 6.28 |
| obs.: | 48.7 | 9.4 | 5.3 | 5.7 |

EXAMPLE 5

N,N'-bis(3-triethoxysilylpropyl)-N,N'-o-phenylene thiourea, $$(C_2H_5O)_3Si-(CH_2)_3-N-CS-N-(CH_2)_3-Si(OC_2H_5)_3, \quad (5)$$

is prepared from 77.5 g N,N'-bis(3-triethoxysilylpropyl)-o-phenylene diamine (15 moles) and 12.6 g carbon disulfide (0.17 mole);

Yield: 79.4 g corresponding to 94.7% g theory;

orange-colored, crystalline solid; $C_{25}H_{46}N_2O_6SSi_2$ (558, 888)

|  | C (%) | H (%) | N (%) | S (%) |
| --- | --- | --- | --- | --- |
| calc.: | 53.73 | 8.30 | 5.01 | 5.74 |
| obs.: | 53.5 | 8.6 | 4.7 | 5.9 |

What is claimed is:

1. N,N,N' and N,N,N',N'-substituted, cyclic thioureas of the general formula (III)

$$(RO)_{3-b}Si-(CH_2)_n-N-R^2-NR^1$$
$$\underset{(CH_3)_b}{|} \diagdown \underset{\underset{S}{\parallel}}{C} \diagup$$

in which n is in the range 1 to 6,

R is alkyl with 1 to 6 carbon atoms, cycloalkyl with 5 to 7 atoms or aryl, $R^1$ is hydrogen or $$-(CH_2)_n-\underset{\underset{(CH_3)_b}{|}}{Si}(OR)_{3-b}$$

$R^2$ is alkylene with 1 to 4 carbon atoms or arylene b is 0,1 or 2.

* * * * *